United States Patent
Metten et al.

(10) Patent No.: US 11,638,680 B2
(45) Date of Patent: May 2, 2023

(54) FIBER CONTAINING HAIR STYLING COMPOSITION

(71) Applicant: Henkel AG & Co. KGaA, Duesseldorf (DE)

(72) Inventors: Diane Metten, Hamburg (DE); Tim Bethge, Oststeinbek (DE); Rene Scheffler, Ellerau (DE); Thorsten Knappe, Schenefeld (DE); Rolf Bayersdoerfer, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 191 days.

(21) Appl. No.: 17/123,313

(22) Filed: Dec. 16, 2020

(65) Prior Publication Data
US 2021/0177707 A1  Jun. 17, 2021

(30) Foreign Application Priority Data
Dec. 17, 2019  (DE) .................... 10 2019 219 794.9

(51) Int. Cl.
| | | |
|---|---|---|
| *A61K 8/02* | (2006.01) | |
| *A61K 8/87* | (2006.01) | |
| *A61K 8/81* | (2006.01) | |
| *A61K 8/34* | (2006.01) | |
| *A61K 8/31* | (2006.01) | |
| *A61K 8/9794* | (2017.01) | |
| *A61Q 5/06* | (2006.01) | |
| *A61K 8/04* | (2006.01) | |
| *A61K 8/9789* | (2017.01) | |

(52) U.S. Cl.
CPC .............. *A61K 8/027* (2013.01); *A61K 8/046* (2013.01); *A61K 8/31* (2013.01); *A61K 8/34* (2013.01); *A61K 8/8147* (2013.01); *A61K 8/87* (2013.01); *A61K 8/9789* (2017.08); *A61K 8/9794* (2017.08); *A61Q 5/06* (2013.01)

(58) Field of Classification Search
CPC .............. A61K 8/027; A61K 8/87; A61Q 5/06
See application file for complete search history.

(56) References Cited

U.S. PATENT DOCUMENTS

2010/0028284 A1* 2/2010 Atis .................... A61Q 1/10
424/70.7
2019/0209445 A1* 7/2019 Torres .................. A61K 8/8135

FOREIGN PATENT DOCUMENTS

| GB | 2580762 A | 7/2020 |
|---|---|---|
| WO | 2020021316 A1 | 1/2020 |

* cited by examiner

*Primary Examiner* — Andrew S Rosenthal
(74) *Attorney, Agent, or Firm* — Lorenz & Kopf, LLP

(57) ABSTRACT

The present disclosure concerns a hair styling composition comprising
(a) at least one component comprising fibers,
b) at least one polymer comprising an acrylate polymer and
c) at least one polymer comprising a polyurethane.

18 Claims, No Drawings

FIBER CONTAINING HAIR STYLING COMPOSITION

CROSS-REFERENCE TO RELATED APPLICATION

This application claims priority to German Patent Application No. 10 2019 219 794.9, filed Dec. 17, 2019, which is incorporated herein by reference in its entirety.

TECHNICAL FIELD

The present disclosure concerns a fiber-containing hair styling composition, a hair styling agent containing this hair styling composition, a container containing the hair styling agent as well as its use and a process for temporarily reshaping and/or increasing the thickness of keratinous fibers.

BACKGROUND

Hair styling compositions for temporary reshaping of keratinous fibers, preferably hair, are known as styling products and are usually applied in the form of gels, pomades, wax, foam, and spray.

Keratinic fibers comprise all fibers containing keratin, such as wool, furs and feathers, especially human hair, with particular emphasis on human hair. During a temporary reshaping of keratinic fibers, no chemical (oxidation and reduction) process takes place. Instead, the fibers are shaped by applying styling products containing strengthening agents such as waxes and/or polymers.

Thick, voluminous hair is still considered an ideal of beauty and a sign of a well-groomed appearance. As a result, consumer demand for styling products that give hair more body and thickness is unbroken.

It is advantageous if the hair looks fuller, i.e. the hair on your head looks as if there are more hairs than there actually are (still) and/or feels fuller or thicker, i.e. when you touch the hair you have the feeling that you have more hair on your head than you have without the styling product.

It is therefore the task of the present disclosure to provide a hair styling composition which gives the hair more fullness both haptically and visually, makes the hair appear thicker and at the same time gives the impression that the user has more hair on his head than is actually present.

BRIEF SUMMARY

This disclosure provides a hair styling composition comprising:
a) at least one component comprising fibers,
b) at least one polymer comprising an acrylate polymer, and
c) at least one polymer comprising a polyurethane.

This disclosure also provides a hair styling composition comprising:
a) at least one component comprising fibers chosen from cotton fibers, flax fibers, bamboo fibers, kapok fibers, and combinations thereof and present in an amount of about 0.5 to about 3.0% by weight based on a total weight of the hair styling composition,
b) at least one polymer comprising an acrylate polymer chosen from compounds with the INCI designation ethylhexyl acrylates/methyl methacrylate copolymer and present in an amount of about 1.5 to about 6% by weight based on a total weight of the hair styling composition,
c) at least one polymer comprising a polyurethane having at least three of the monomer units chosen from propylene glycol, ethylene glycol, 4,4-MDI, 2,4-MDI, 2,2-MDI and mixtures thereof and present in an amount of about 0.5 to about 4% by weight based on a total weight of the hair styling composition, and
a monohydric alcohol chosen from methanol, ethanol, n-propanol, iso-propanol, n-butanol, isobutanol, tert-butanol, pentanol, and combinations thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task is solved by a hair styling composition comprising
(a) at least one component comprising fibers,
b) at least one polymer comprising an acrylate polymer and
c) at least one polymer comprising a polyurethane.

Hair styling composition means a cosmetic hair styling composition, which can be formulated in common forms of hair styling compositions, preferably the hair styling composition is sprayable, especially preferably it is formulated as spray.

Preferably, the hair styling composition comprises at least one component comprising fibers.

The fibers are stretched to square, flexible structures of fibrous material with a length to diameter ratio of about 10:1, preferably of about 5:1 and especially of about 3:1, especially of from about 2:1 to about 1:1. In the longitudinal direction, fibers can only absorb tensile forces, not compressive forces.

The length of preferably used fibers ranges from about 1 to about 200 µm, preferably from about 2 to about 150 µm and especially from about 5.0 to about 100 µm. In a configuration of the present disclosure, fibers with a longer fiber length, for example fibers with a length above about 200 µm or above about 300 µm, can also be used.

The fiber material can be of natural or synthetic origin. Natural fibers are all those fibers which are obtained from plant, animal, or mineral material without chemical modification.

Plant fibers are found in plants as vascular bundles in the stem, in the stem, in the bark or as seed appendages. Plant fibers usually consist mainly of cellulose. Corresponding fibers are summarized under the designation cellulose fibers.

According to a widespread subdivision, plant fibers are divided into seed fibers, bast fibers, leaf fibers and fruit fibers. Cotton fibers, kapok, acon or poplar fluff belong to the group of seed fibers. The group of bast fibers includes bamboo fiber, nettle fiber, hemp fiber, jute, and flax fiber. Sisal belongs to the leaf fibers, while coconut fibers belong to the group of fruit fibers. Bamboo fibers are also suitable.

Among animal fibers, a distinction can be made between fibers from spinning glands and fibers derived from hair follicles. Silk is one of the fibers from spinning glands. The group of fibers originating from hair follicles includes wool, alpaca, camel hair, angora, cashmere, mohair, yak hair, goat hair, cow hair or horsehair.

In a preferred design, the fibers used in hair styling compositions are selected from the group of fibers from natural fiber materials. The use of cellulose fibers, especially cotton fibers, flax fibers and kapok fibers is particularly preferred. The use of animal fibers from the group of silk fibers, cashmere fibers and wool fibers is also preferred. The use of cellulose fibers is particularly preferred.

Alternatively, or in combination with the natural fibers described above, fibers based on synthetic fiber materials can also be used in hair styling compositions.

The use of synthetic fiber materials obtained by modification of plant or animal starting materials is particularly preferred. The group of these preferred fibers includes fibers made of viscose, polylactic acid, alginate, chitin, or chitosan.

Other preferred synthetic fiber materials are polyamides, polyesters and polyhydroxyalkanoates.

Preferably, the at least one component comprising fibers, with a proportion of from about 0.05 to about 5.0% by weight, preferably from about 0.1 to about 4.0% by weight, even more preferably from about 0.3 to about 3.5% by weight, most preferably from about 0.5 to about 3.0% by weight, measured on the total proportion of the hair styling composition.

Preferably, the hair styling composition comprises at least one component comprising an acrylic polymer.

An acrylate copolymer in the context of this application comprises at least two different monomers, one of which is necessarily an acrylate or methacrylate. Acrylate is a collective term for substances that are chemically exemplified by the acrylic group (CH2=CH—COR) (depending on R, it can be acrylic acid or the salts or esters of acrylic acid). Methacrylate accordingly have a methacrylic group (CH3CH=CH—COR).

It is particularly preferred that the at least one polymer contains an acrylate copolymer obtained by reacting ethylhexyl acrylate with methyl methacrylate. Preferred acrylate copolymers are selected from the group with the INCI designation Ethylhexyl Acrylate/Methyl Methacrylate Copolymer.

Such an acrylate copolymer is available, for example, under the designation "Eurocryl BC 4365 HE" (INCI: Ethylhexyl Acrylate/Methyl Methacrylate Copolymer, active substance: about 50 weight % in water).

Preferably the at least one polymer comprising an acrylate polymer, with a proportion of from about 0.1 to about 10.0% by weight, preferably from about 0.5 to about 8.0% by weight, even more preferably from about 1.0 to about 7.0% by weight, even more preferably from about 1.5 to about 6.0% by weight, measured on the total proportion of the hair styling composition.

Preferably, the hair styling composition comprises at least one component comprising a polyurethane.

In a preferred embodiment of the present disclosure, the polymer comprising a polyurethane has at least two, preferably three of the monomer units selected from methylene diphenyl isocyanate (4,4'-diphenylmethane diisocyanate or MDI for short), propylene glycol (PPG for short), ethylene glycol (PEG for short), 2,4-MDI, 2,2-MDI and mixtures thereof.

In particular, the polymer comprising a polyurethane has at least one of the monomer units selected from methylene diphenyl isocyanate (4,4'-diphenylmethane diisocyanate or MDI for short), 2,4-MDI and 2,2-MDI and at least one, preferably two of the monomers selected from propylene glycol and ethylene glycol.

Preferably, the ethylene glycol has from about 3 to about 20, particularly preferably from about 5 to about 15, most preferably from about 7 to about 12 repeat units.

Preferably, propylene glycol has from about 3 to about 20, particularly preferably from about 4 to about 13, most preferably from about 5 to about 10 repeat units.

In a special configuration of the present disclosure, the at least one polymer comprising polyurethane has the INCI PEG-9/PPG-7/MDI copolymer on it.

Preferably the at least one polymer comprising a polyurethane in a proportion of from about 0.01 to about 5.5-% by weight, preferably from about 0.05 to about 5.0% by weight, even more preferably from about 0.1 to about 4.5% by weight, most preferably from about 0.5 to about 4.0% by weight, measured on the total proportion of the hair styling composition.

Preferably the hair styling composition contains at least one monohydric alcohol, preferably selected from methanol, ethanol, n-propanol, iso-propanol, n-butanol, isobutanol, tert-butanol and pentanol, particularly preferably selected from ethanol, n-propanol and iso-propanol, particularly preferably ethanol.

The at least one monohydric alcohol acts as a cosmetically acceptable carrier component of the hair styling composition. Preferably the at least one monohydric alcohol with a proportion of from about 50.0 to about 98.0% by weight, preferably from about 75.0 to about 95.0% by weight, even more preferably from about 75.0 to about 93.0% by weight, most preferably from about 80.0 to about 90.0% by weight in the hair styling composition, measured on the total proportion of the hair styling composition.

Polymers are used in cosmetic hair styling compositions, for example because of their firming and/or film-forming properties. Due to their cosmetic effect, the use of film-forming polymers is particularly preferred. The use of polymers with thickening effect, with hair texturing effect, with hair caring effect and/or with hair conditioning effect can also be advantageous.

Preferably, the hair styling composition contains at least one additional polymer. Permanent as well as temporary cationic, anionic, non-ionic, or amphoteric polymers are suitable as further polymers. The other polymers can be of synthetic or natural origin.

Examples of other polymers are Acrylamides/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/Ammonium Methacrylate Copolymer Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Acid/Neopentyl Acid of/Trimethylolpropane Copolymer, Allyl Stearate/VA Copolymer, Aminoethyl acrylate Phosphate/Acrylates Copolymer, Aminoethylpropanediol-Acrylates/Acrylamide Copolymer, Aminoethylpropanediol-AMPD-Acrylates/Diacetone Acrylamide Copolymer, Ammonium VA/Acrylates Copolymer, AMPD-Acrylates-Acrylates-Diacetone Allyl Methacrylate Copolymer, AMP-Acrylates/C1-

18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, Bacillus/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutyl methacrylate/Bis-Hydroxypropyl Dimethicone Acrylate Copolymer, Isopropyl Ester of PVMyl/MA Acrylate Copolymer, Laurel Crosspolymer, Lauryl Methacrylate/Glycol Dimethacrylate Crosspolymer, MEA-Sulphite, Methacrylic Acid/Sodium Acrylamidomethyl Propane Sulphonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenquaternium-2-Polyquaternium-2-Polyquaternium, Polyperfluoroperhydrophenanthrenium 4, Polyquaternium-5, Polyquaternium-6, Polyquaternium-7, Polyquaternium-8, Polyquaternium-9, Polyquaternium-10, Polyquaternium-11, Polyquaternium-12, Polyquatemium-13, Polyquatemium-14, Polyquaternium-15, Polyquaternium-16, Polyquaternium-17, Polyquaternium 18, Polyquatemium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquatemium-55, Polyquaternium-56, Polysilicone-9, Polyvinyl Acetate-9, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI copolymer, PPG-10 sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Copolymer, Crodonates/VA Copolymer/Abenzanoate, VA Copolymer Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethyl methacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

The other polymer selected from the group of non-ionic or temporarily cationic polymers is of advantage. Suitable polymers are for example:

Polyvinyl acetates, such as those marketed under the name Vinnapas®,

Cellulose ethers, such as hydroxypropyl cellulose (HPC), hydroxyethyl cellulose (HEC) and hydroxypropyl methyl cellulose (HPMC), such as those marketed under the name Affinisol by Dow Pharma Solutions, Copolymers of methyl vinyl ether and maleic anhydride, especially their esters such as those marketed under the name Omnirez 2000 (INCI: Ethyl Ester of PVM/MA Copolymer) from Ashland, other acrylate copolymers such as in particular a copolymer with the INCI designation Acrylates/Hydroxyesters Acrylates Copolymer organosilicon polymer compound, such as a compound with the INCI name Crotonic Acid/Vinyl C8-12 Isoalkyl Esters/VA/Bis-Vinyldimethicone crosspolymer, which is provided by Wacker as a about 50% solution in denatured ethanol under the name BELSIL® P 1101, Polyethylene glycols, such as in particular PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-350, PEG-400, PEG-500, PEG-800, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M or PEG-180M.

Preferred are hair styling compositions in which the at least one other polymer is selected from polyvinyl acetate, a copolymer with the INCI designation Castor Oil/IPDI Copolymer, cellulose ether, siloxanes, polyethylene glycols, a copolymer with the INCI designation Acrylates/Hydroxyesters Acrylates Copolymer, copolymers of methyl vinyl ether and maleic anhydride, a copolymer having the INCI designation crotonic acid/vinyl C8-12 isoalkyl esters/VA/bis-vinyl dimethicone crosspolymer, a copolymer having the INCI vinyl caprolactam/VP/dimethylaminoethyl methacrylate copolymer or the INCI vinyl caprolactam/VP/dimethylaminoethyl methacrylate copolymer (and) lauryl pyrrolidones, and mixtures thereof.

It is particularly preferred that the hair styling composition comprises as at least one further polymer a polyethylene glycol, preferably selected from PEG-20, PEG-25, PEG-30, PEG-35, PEG-40, PEG-45, PEG-50, PEG-55, PEG-60, PEG-65, and PEG-70, particularly preferably from PEG-25 to PEG-65, most preferably from PEG-30 to PEG-40, particularly preferably PEG-32.

It has been shown that the use of polyethylene glycol, such as PEG-32, results in a hair styling composition that has a positive texturing effect when applied to keratinous fibers.

In a configuration of the present disclosure, the hair styling composition contains polyethylene glycols (PEG) which can be described by the general formula H—(O—CH2-CH2)n-OH PEGs have a degree of polymerization n of about 5 up to <about 100,000, corresponding to molar masses of from about 200 to about 5,000,000 gmol-1. Products with molecular masses below about 25,000 gmol-1 are referred to as actual polyethylene glycols, while higher molecular weight products are often referred to in the literature as polyethylene oxides (PEOX for short).

The polyethylene glycols preferably used can have a linear or branched structure, linear polyethylene glycols being particularly preferred.

The preferred polyethylene glycols have relative molecular masses in the range of from about 750 and about 3500, preferably from about 900 to about 3000, even more preferably from about 1000 to about 2500, especially preferred from about 1500 to about 2100.

Preferably the at least one polyethylene glycol with a proportion of from about 0.05 to about 5.0% by weight, preferably from about 0.1 to about 4.0% by weight, even more preferably from about 0.5 to about 3.0% by weight, even more preferably from about 1.0 to about 2.5% by weight, measured on the total proportion of the hair styling composition.

In another preferred embodiment of the present disclosure, the hair styling composition comprises a polyvinyl acetate (homopolymer of vinyl acetate) as another polymer.

Preferably the at least one polyvinyl acetate with a proportion of from about 0.05 to about 5.0% by weight, preferably from about 0.1 to about 4.0% by weight, even more preferably from about 0.5 to about 3.0% by weight, even more preferably from about 1.0 to about 2.0% by weight, measured on the total proportion of the hair styling composition.

In another preferred embodiment of the present disclosure, the hairstyling composition comprises as a further polymer a cellulose ether, preferably hydroxypropyl methylcellulose (HPMC).

Preferably the at least one cellulose ether with a proportion of from about 0.01 to about 2.5% by weight, preferably from about 0.03 to about 2.0% by weight, even more preferably from about 0.05 to about 1.0% by weight, most preferably from about 0.1 to about 1.0% by weight in the hair styling composition, measured on the total proportion of the hair styling composition.

In a further preferred embodiment of the present disclosure, the hair styling composition comprises as a further polymer a polymer with the INCI Vinyl Caprolactam/VP/Dimethylaminoethyl Methacrylate Copolymer or the INCI Vinyl Caprolactam/VP/Dimethylaminoethyl Methacrylate copolymer (and) Lauryl Pyrrolidone.

Preferably at least one polymer with the INCI Vinyl Caprolactam/VP/Dimethylaminoethyl Methacrylate Copolymer or the INCI Vinyl Caprolactam/VP/Dimethylaminoethyl Methacrylate copolymer (and) Lauryl Pyrrolidone with a proportion of from about 0.05 to about 5.0 wt.-%, preferably from about 0.1 to about 4.0 wt. %, even more preferably from about 0.5 to about 3.0 wt. %, even more preferably from about 1.0 to about 2.0 wt. % in the hair styling composition, measured on the total proportion of the hair styling composition.

Accordingly, hair styling compositions with one of the following combinations of other polymers are preferred:
- at least one polyethylene glycol and at least one polyvinyl acetate,
- at least one polyethylene glycol, at least one polyvinyl acetate and at least one cellulose ether,
- at least one polyethylene glycol, at least one polyvinyl acetate and at least one polymer with the INCI vinyl caprolactam/VP/dimethylaminoethyl methacrylate copolymer (and) lauryl pyrrolidone,
- at least one polyethylene glycol, at least one polyvinyl acetate, at least one cellulose ether and at least one polymer with the INCI vinyl caprolactam/VP/dimethylaminoethyl methacrylate copolymer (and) lauryl pyrrolidone,
- at least one polyethylene glycol and at least one polymer with the INCI Vinyl Caprolactam/VP/Dimethylaminoethyl Methacrylate copolymer (and) Lauryl Pyrrolidone
- at least one polyvinyl acetate and at least one polymer with the INCI vinyl caprolactam/VP/dimethylaminoethyl methacrylate copolymer (and) lauryl pyrrolidone.

The hair styling composition may also contain other components selected from preservatives, humectants, pH adjustment agents, conditioning agents, perfume, pigments, surfactants, and mixtures thereof.

The hair styling composition at least one care component.

Preferably the at least one care component comprises a care oil and/or at least one care ingredient, wherein the at least one care oil comprises a triglyceride of native origin. Particularly preferential are vegetable care oils selected from Amaranth seed oil, Argan oil, rice germ oil, Baobab oil, Manetti oil, Marula seed oil, Yangusamen oil, Rambutan oil, Buckthorn oil, Monoi de Tahiti, tiger nut oil, Inca Inchi Oil, avocado oil, cotton seed oil, Cupuagu butter, Cashew oil, Safflower oil, peanut oil, jojoba oil, chamomile oil, coconut oil, pumpkin seed oil, linseed oil, macadamia oil, corn germ oil, almond oil, apricot kernel oil, poppy seed oil, evening primrose oil, olive oil, rapeseed oil, soybean oil, sunflower oil and wheat germ oil, in particular (−)-α-bisabolol, hydrogenated jojoba oil and/or coconut oil. Further preferred are care components selected from vitamins, provitamins, vitamin precursors and/or their derivatives. Preference is given to vitamins, provitamins and vitamin precursors that are usually assigned to groups A, B, C, E, F and H. A particularly preferred care ingredient is D-panthenol.

As a care component, the hair styling composition may also contain at least one protein hydrolysate and/or one of its derivatives. Protein hydrolysates are product mixtures obtained by acidic, basic, or enzymatic catalyzed degradation of proteins. As contemplated herein, the term protein hydrolysates also includes total hydrolysates as well as individual amino acids and their derivatives and mixtures of different amino acids. The molecular weight of the protein hydrolysates that can be used as contemplated herein is between about 75, the molecular weight for glycine, and about 200,000, preferably the molecular weight is from about 75 to about 50,000 and most preferably from about 75 to about 20,000 daltons.

Preferably, the at least one care component with a proportion of from about 0.01 to about 1.0% by weight, preferably from about 0.03 to about 0.7% by weight, even more preferably from about 0.04 to about 0.5% by weight, most preferably from about 0.06 to about 0.3% by weight, is contained in the hair styling composition, measured on the total proportion of the hair styling composition.

Preferably, the hair styling composition contains at least one anionic, cationic, amphoteric, or nonionic surfactant.

Examples of anionic surfactants are soaps, alkylbenzene sulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, Mono- and dialkyl sulfosuccinamates, sulfotriglyceride, amide soaps, ether carboxylic acids and their salts, fatty acid isethionates, fatty acid sarcosinates, fatty acid taurides, N-acyl amino acids, such as acyl lactylates, acyl tartrates, acyl glutamates and acyl spartates, alkyl oligoglucoside sulfates, protein fatty acid condensates (especially wheat-based vegetable products) and alkyl (ether) phosphates. If the anionic surfactants contain polyglycol ether chains, they may have a conventional, but preferably a narrowed homologue distribution. Examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed-formal, optionally partially oxidized alk(en)yl oligoglycosides or glucoronic acid derivatives, fatty acid-N-alkyl glucamides, protein hydrolysates (in particular wheat-based vegetable products), polyol fatty acid esters, sugar esters, sorbitan esters, polysorbates and amine oxides. If the non-ionic surfactants contain polyglycol ether chains, they may have a conventional, but preferably a narrowed homologue distribution. Examples of cationic surfactants are quaternary ammonium compounds and esterquats, especially quaternized fatty acid trialkanolamine ester salts. Preferred quaternary ammonium compounds are again ammonium halides, especially chlorides and bromides, such as alkyl trimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations quaternium-27 and quaternium-83. The use of cetyltrimethylammonium chloride is particularly preferred.

The at least one amphoteric surfactant selected from alkylbetaines, alkylamidobetaines, aminopropionates, aminoglycinates, imidazoliniumbetaines, sulfobetaines and mixtures thereof. Amphoteric or also zwitterionic surfactants carry both a cationic and an anionic charge in the molecule. Preferably, amphoteric surfactants have at least one quaternary ammonium group and at least one —COO(—)- or —SO3(-)-group, in addition to a preferably C8-C24 alkyl or acyl group, in the molecule. They are also capable of forming inner salts. Particularly preferred amphoteric surfactants are betaines such as the N-alkyl-N,N-dimethylammoniumglycinate, for example the cocoalkyl-dimethyl-ammoniumglycinate, N-acylaminopropyl-N,N-dimethylammoniumglycinate, for example the cocoacylaminopropyl dimethyl ammonium glycinate, and 2-alkyl-3-carboxymethyl-3-hydroxyethyl imidazolines each having 8 to 18 C atoms in the alkyl or acyl group, and the cocoacylaminoethyl hydroxyethyl carboxymethyl glycinate. A preferred amphoteric surfactant is the fatty acid amide derivative known under the INCI name cocamidopropyl betaine. With regard to the structure and manufacture of these substances, reference is made to relevant reviews, e.g. J. Falbe (ed.), "Surfactants in Consumer Products", Springer Verlag, Berlin, 1987, pp. 54-124 or J. Falbe (ed.), "Katalysatoren, Tenside and Mineralöladditive/Catalysts, surfactants and mineral oil additives", Thieme Verlag, Stuttgart, 1978, pp. 123-217.

Preferably the at least one anionic, cationic, amphoteric or nonionic surfactant, particularly preferably the at least one amphoteric surfactant with a proportion of from about 0.01 to about 3.0% by weight, preferably from about 0.05 to about 1.5% by weight, even more preferably from about 0.1 to about 1.0% by weight, very particularly preferably from about 0.3 to about 0.7% by weight, in the hair styling composition, measured on the total proportion of the hair styling composition.

Furthermore, the hairstyling composition may contain agents for pH adjustment. Preferred agents are for example primary amino alcohols such as aminomethyl propanol (INCI), which is commercially available under the name AMP-ULTRA© PC, for example AMP-ULTRA© PC 2000. Other pH adjusting agents may be selected from alkaline hydroxides, in particular sodium hydroxide and potassium hydroxide, organic acids such as lactic acid, citric acid, hydrochloric acid, sulphuric acid, phosphoric acid, adipic acid, malic acid, succinic acid, succinic acid, tartaric acid or malic acid, in particular tetrahydroxypropyl ethylenediamine known under the trade names Neutrol TE and triethylamine (TEA).

The proportion of pH adjustment agents in the hair styling composition is preferably from about 0.01 to about 3.5% by weight, particularly preferably from about 0.05 to about 2.5% by weight, very preferably from about 0.1 to about 02.0% by weight, even more preferably from about 0.5 to about 1.7% by weight, based on the total proportion of the hair styling composition.

Furthermore, the hairstyling composition may contain a preservative, in particular those listed in the Regulation on cosmetic products in Annex V (Regulation (EC) No 122+3/2009 of the European Parliament and of the Council of 30 Nov. 2009 on cosmetic products), particularly preferably benzoic acid, benzoates and mixtures thereof, particularly preferably sodium benzoate.

The proportion of preservatives in the hair styling composition is preferably from about 0.01 to about 2.0% by weight, more preferably from about 0.05 to about 0.6% by weight, more preferably from about 0.1 to about 0.5% by weight, based on the total proportion of the hair styling composition.

In a further embodiment of the present disclosure, the hair styling composition contains at least one cosmetically acceptable perfume and/or at least one plant extract. Preferred is at least one other plant extract selected from bamboo extract (*Bambusa Vulgaris*), birch sap, coconut milk, hop extract, avocado extract, chamomile extract and mixtures of these. Also suitable are the extracts and/or exudates from plants or parts of plants of green tea, oak bark, nettle, witch hazel, burdock root, horsetail, hawthorn, lime blossom, lychee, almond, aloe vera, spruce needle, horse chestnut, sandalwood, juniper, coconut, mango, Apricot, lime, wheat, kiwi, melon, orange, grapefruit, sage, rosemary, mallow, cuckoo flower, thyme, lemon balm, cowslip, marshmallow, ginseng, *ginger* root, *Echinacea purpurea, Olea europea, Boerhavia diffusa* roots, *Foeniculum vulgaris* and *Apim graveolens*.

Preferably the at least one other plant extract with a proportion of from about 0.001 to about 1.0% by weight, preferably from about 0.002 to about 0.5% by weight, particularly preferably from about 0.002 to about 0.01% by weight, even more preferably from about 0.003 to about 6.5% by weight, based on the total proportion of the hair styling composition, in the hair styling composition.

Further, the present disclosure relates to a hair styling agent comprising a hair styling composition as contemplated herein and a blowing agent.

Preferably, the hair styling product is preferably available as a spray. For this purpose, the hair styling products are packaged in a dispensing device, which is either a compressed gas container additionally filled with a propellant ("aerosol container") or a non-aerosol container. The pressurized gas containers, with the help of which a product is distributed by the internal gas pressure of the container via a valve, are called "aerosol containers". A "non-aerosol container" is defined, in reverse to the aerosol definition, as a container under normal pressure with the aid of which a product is distributed by mechanical action through a pumping or squeezing system.

Preferred propellants (propellant gases) are all gases permitted for cosmetic hair styling compositions, in particular selected from propane, propene, n-butane, iso-butane, iso-butene, 2-methylbutane, n-pentane, pentene, iso-pentane, iso-pentene, methane, ethane, dimethyl ether, nitrogen, Air, oxygen, nitrous oxide, dichlorofluoromethane, chlorodifluoromethane, chlorofluoromethane, 1,2,2-tetrachloro-1-fluoroethane, 1,1,2-tetrachloro-2-fluoroethane, 1,2,2-trichloro-1,1-difluoroethane, 1,1,2-trichloro-1,2-difluoroethane, 1,1,1-trichloro-2,2-difluoroethane, 2,2-dichloro-1,1,1-trifluoroethane, 1,2-dichloro-1,1,2-trifluoroethane, 2-chloro-1,1,1,2-tetrafluoroethane, 1-chloro-1,1,2,2-tetrafluoroethane, 1,1,2-trichloro-2-fluoroethane, 1,2-dichloro-1,2-difluoroethane, 1,2-dichloro-1,1-difluoroethane, 1-chloro-1,2,2-trifluoroethane, 2-chloro-1,1,1-trifluoroethane, 1-chloro-1,2-trifluoroethane, 1,2-Dichloro-1-fluoroethane, 1,1-dichloro-1-fluoroethane, 2-chloro-1,1-difluoroethane, 1-chloro-1,1-difluoroethane, 1-chloro-2-fluoroethane, 1-chloro fluoroethane 2-chloro-1,1-difluoroethene, 1,1,1,3-tetrafluoroethane, heptafluoro-n-propane, perfluoroethane, monochlorodifluoromethane, 1,1-difluoroethane and mixtures thereof.

Preferred is the use of propane, propane/butane mixtures or dimethyl ether, especially preferred is the use of dimethyl ether.

Preferably the at least one blowing agent with a proportion of from about 50.0 to about 90.0% by weight, preferably from about 55.0 to about 85.0% by weight, particularly preferably from about 60.0 to about 80.0% by weight, even more preferably from about 65.0 to about 75.0% by weight, based on the total proportion of the hair styling composition, in the hair styling composition.

With a given spraying device, the sizes of the foam bubbles and the respective size distribution can be adjusted via the quantity ratio of blowing agent to the other components of the preparations.

Aerosol dispensing containers are particularly suitable for dispensing and applying the hair styling product. A further object of the application is the corresponding delivery container, comprising
a) a hair styling agent as contemplated herein and
(b) an aerosol dispenser.

The term aerosol dispenser is used to describe pressure vessels in whose interior there is a higher gas pressure than outside the vessel and from which a gas flow can be withdrawn via a valve. In other words, aerosol dispensers are pressure vessels that allow a product (e.g. a cosmetic hairstyling composition) to be dispensed by the internal gas pressure of the container through a valve.

The cosmetic hair styling compositions can be produced in the usual way. As a rule, all ingredients of the cosmetic hairstyling composition are used except for the
Propellant is filled into a suitable pressure-resistant container. This is then closed with a valve. Using conventional techniques, the desired amount of blowing agent is then added.

Pressure-resistant containers can be vessels made of metal (aluminum, tinplate, tin), protected or non-splintering plastic or glass, coated on the outside with plastic. The selection of pressure-resistant containers must consider resistance to pressure and breakage, corrosion resistance, ease of filling as well as aesthetic aspects, ease of handling, printability, etc. Special internal protective coatings ensure corrosion resistance to the hairstyling composition assembled in the pressure vessel. In particular, the valves used have an internally painted valve head, whereby the paint and valve material are compatible with each other. If aluminum valves are used, their valve disks can be coated on the inside with Micoflex lacquer, for example. If tinplate valves are used as contemplated herein, their valve disks can be coated on the inside with PET (polyethylene terephthalate), for example.

A multi-chamber dispenser can also be used as an aerosol dispensing container. The multi-chamber dispenser may also be designed so that one chamber is filled with the compressed blowing agent and another chamber is filled with the remaining ingredients of the hair styling composition of the present disclosure. One such multi-chamber dispenser is a so-called bag-in-can packaging.

The spray rate of cosmetic hair styling products is preferably from about 6.5 to about 12 g/10 s, preferably from about 7.5 to about 11 g/10 s.

Another subject of this application is a process for the temporary deformation of keratinous fibers, in particular human hair, in which a hair styling composition and/or hair styling agent as contemplated herein is applied to keratinous fibers. The ingredients of this hairstyling composition, their proportions by weight and preferred forms of execution shall apply mutatis mutandis to the foregoing.

Another subject-matter of this application is a process for increasing the thickness of keratinous fibers, human hair, in which a hair styling composition and/or hair styling agent of the present disclosure is applied to keratinous fibers. The ingredients of this hairstyling composition, their proportions by weight and preferred forms of execution shall apply mutatis mutandis to the foregoing. Keratinous fibers can also be advantageously remodeled or restyled if they have been combed after application of the hair styling composition and/or hair styling products as contemplated herein. Increasing the thickness means as contemplated herein that the keratinic fibers appear optically and/or haptically thicker than before the application of the described process.

It has also been shown to be advantageous that hairstyles made with a straightening iron and/or curling iron, such as straightening or curling, have a longer hold than with conventional styling products. Furthermore, the waves/curls have a better bounce.

Furthermore, the present disclosure comprises the use of a hair styling composition and/or the hair styling agent as contemplated herein for temporary reshaping and/or form-fixing, remodeling of keratinous fibers, preferably human scalp hair.

Furthermore, the present disclosure comprises the use of a hair styling composition as contemplated herein and/or the hair styling agent as contemplated herein for increasing the thickness of keratinous fibers, of human hair.

WORKED EXAMPLE

Some more preferred hair styling compositions can be found in the following tables (percentages by weight based on the total weight of the hair styling composition unless otherwise stated).

| Components | Formula 1 | Formula 2 | Formula 3 | Formula 4 | Formula 5 |
|---|---|---|---|---|---|
| at least one component comprising fibers | 0.05-5.0 | 0.1-4.0 | 0.3-3.5 | 0.5-3.0 | 1.0-2.0 |

-continued

| Components | | | | | |
|---|---|---|---|---|---|
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |

| Components | Formula 6 | Formula 7 | Formula 8 | Formula 9 | Formula 10 |
|---|---|---|---|---|---|
| Cellulose | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |

| Components | Formula 11 | Formula 12 | Formula 13 | Formula 14 | Formula 15 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |

| Components | Formula 16 | Formula 17 | Formula 18 | Formula 19 | Formula 20 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |

| Components | Formula 21 | Formula 22 | Formula 23 | Formula 24 | Formula 25 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |

| Components | Formula 26 | Formula 27 | Formula 28 | Formula 29 | Formula 30 |
|---|---|---|---|---|---|
| Cellulose | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |

| Components | Formula 31 | Formula 32 | Formula 33 | Formula 34 | Formula 35 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |

-continued

| Components | Formula 36 | Formula 37 | Formula 38 | Formula 39 | Formula 40 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |

| Components | Formula 41 | Formula 42 | Formula 43 | Formula 44 | Formula 45 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| Ethanol | 50.0-98.0 | 75.0-93.0 | 75.0-90.0 | 78.0-88.0 | 80.0-86.0 |

| Components | Formula 46 | Formula 47 | Formula 48 | Formula 49 | Formula 50 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |

| Components | Formula 51 | Formula 52 | Formula 53 | Formula 54 | Formula 55 |
|---|---|---|---|---|---|
| Cellulose | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |

| Components | Formula 56 | Formula 57 | Formula 58 | Formula 59 | Formula 60 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |

| Components | Formula 61 | Formula 62 | Formula 63 | Formula 64 | Formula 65 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |

-continued

| Components | Formula 66 | Formula 67 | Formula 68 | Formula 69 | Formula 70 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| Ethanol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |

| Components | Formula 71 | Formula 72 | Formula 73 | Formula 74 | Formula 75 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| Ethanol | 50.0-98.0 | 75.0-93.0 | 75.0-90.0 | 78.0-88.0 | 80.0-86.0 |
| PEG-32 | 0.05-5.0 | 0.1-4.0 | 0.5-3.0 | 1.0-2.0 | 1.4-1.9 |

| Components | Formula 76 | Formula 77 | Formula 78 | Formula 79 | Formula 80 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |

| Components | Formula 81 | Formula 82 | Formula 83 | Formula 84 | Formula 85 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/ Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| Ethanol | 50.0-98.0 | 75.0-93.0 | 75.0-90.0 | 78.0-88.0 | 80.0-86.0 |
| PEG-32 | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |

| Components | Formula 86 | Formula 87 | Formula 88 | Formula 89 | Formula 90 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |
| Cellulose Ethers | 0.01-2.5 | 0.05-2.0 | 0.1-1.5 | 0.3-1.0 | 0.4-0.7 |

| Components | Formula 91 | Formula 92 | Formula 93 | Formula 94 | Formula 95 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |

| Components | Formula 96 | Formula 97 | Formula 98 | Formula 99 | Formula 100 |
|---|---|---|---|---|---|
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |
| Hydroxypropyl methylcellulose (HPMC) | 0.01-2.5 | 0.05-2.0 | 0.1-1.5 | 0.3-1.0 | 0.4-0.7 |

| Components | Formula 96 | Formula 97 | Formula 98 | Formula 99 | Formula 100 |
|---|---|---|---|---|---|
| Cellulose | 0.05-5.0 | 0.1-4.0 | 0.3-3.5 | 0.5-3.0 | 1.0-2.0 |
| Ethylhexyl Acrylate/Methyl Methacrylate Copolymer | 0.1-10.0 | 0.5-8.0 | 1.0-7.0 | 1.5-6.0 | 4.0-6.0 |
| PEG-9/PPG-7/MDI Copolymer | 0.01-5.0 | 0.05-4.5 | 0.1-4.0 | 0.5-3.5 | 2.0-3.5 |
| Ethanol | 50.0-98.0 | 75.0-93.0 | 75.0-90.0 | 78.0-88.0 | 80.0-86.0 |
| PEG-32 | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |
| Cellulose ether, preferably hydroxypropyl methylcellulose (HPMC) | 0.01-2.5 | 0.05-2.0 | 0.1-1.5 | 0.3-1.0 | 0.4-0.7 |

| Components | Formula 101 | Formula 102 | Formula 103 | Formula 104 | Formula 105 |
|---|---|---|---|---|---|
| at least one component comprising fibers | 0.05-5.0 | 0.1-4.0 | 0.3-3.5 | 0.5-3.0 | 1.0-2.0 |
| at least one polymer comprising an acrylate polymer | 0.1-10.0 | 0.5-8.0 | 1.0-7.0 | 1.5-6.0 | 4.0-6.0 |
| at least one polymer comprising a polyurethane | 0.01-5.0 | 0.05-4.5 | 0.1-4.0 | 0.5-3.5 | 2.0-3.5 |
| monohydric alcohol | 50.0-98.0 | 75.0-93.0 | 75.0-90.0 | 78.0-88.0 | 80.0-86.0 |
| Polyethylene glycol | 0.05-5.0 | 0.1-4.0 | 0.5-3.0 | 1.0-2.0 | 1.4-1.9 |
| Polyvinyl acetate | 0.05-5.0 | 0.1-4.0 | 0.5-3.0 | 1.0-2.0 | 1.4-1.9 |
| Cellulose Ethers | 0.01-2.5 | 0.05-2.0 | 0.1-1.5 | 0.3-1.0 | 0.4-0.7 |
| Vinyl-Caprolactam/VP/Dimethyl aminoethylmethacrylate-Copolymer [(und) Laurylpyrrolidon] | 0.05-5.0 | 0.1-4.0 | 0.5-3.0 | 1.0-2.0 | 1.4-1.9 |

Some more preferred hair styling products, containing the hair styling composition and a propellant, can be found in the following tables (data in % by weight based on the total weight of the hair styling composition, unless otherwise stated).

| Components | Formula 106 | Formula 107 | Formula 108 | Formula 109 | Formula 110 |
|---|---|---|---|---|---|
| Formula 1 | 10.0-50.0 | | | | |
| Formula 16 | | 10.0-50.0 | | | |
| Formula 26 | | | 10.0-50.0 | | |
| Formula 30 | | | | 10.0-50.0 | |
| Formula 46 | | | | | 10.0-50.0 |
| Blowing agent, preferably dimethyl ether or mixture comprising at least propane and butane | 50.0-90.0 | 55.0-85.0 | 60.0-80.0 | 65.0-75.0 | 68.0-73.0 |

| Components | Formula 111 | Formula 112 | Formula 113 | Formula 114 | Formula 115 |
|---|---|---|---|---|---|
| Formula 50 | 10.0-50.0 | | | | |
| Formula 66 | | 10.0-50.0 | | | |
| Formula 70 | | | 10.0-50.0 | | |
| Formula 71 | | | | 10.0-50.0 | |
| Formula 75 | | | | | 10.0-50.0 |
| Blowing agent, preferably dimethyl ether or mixture comprising at least propane and butane | 50.0-90.0 | 55.0-85.0 | 60.0-80.0 | 65.0-75.0 | 68.0-73.0 |

| Components | Formula 116 | Formula 117 | Formula 118 | Formula 119 | Formula 120 |
|---|---|---|---|---|---|
| Formula 81 | 10.0-50.0 | | | | |
| Formula 86 | | 10.0-50.0 | | | |
| Formula 91 | | | 10.0-50.0 | | |
| Formula 96 | | | | 10.0-50.0 | |
| Formula 102 | | | | | 10.0-50.0 |
| Blowing agent, preferably dimethyl ether or mixture comprising at least propane and butane | 50.0-90.0 | 55.0-85.0 | 60.0-80.0 | 65.0-75.0 | 68.0-73.0 |

-continued

| Components | Formula 121 | Formula 122 | Formula 123 | Formula 124 | Formula 125 |
| --- | --- | --- | --- | --- | --- |
| Sensocel bc 20* | 0.01-3.0 | 0.03-2.5 | 0.05-2.0 | 0.1-1.0 | 0.2-0.9 |
| Eurocryl BC 4365** | 0.05-4.5 | 0.1-4.0 | 0.5-3.0 | 0.8-2.5 | 1.0-2.4 |
| PEG-9/PPG-7/MDI Copolymer | 0.01-5.0 | 0.05-4.5 | 0.1-3.0 | 0.3-2.5 | 0.4-2.2 |
| Ethanol (96%) | 10.0-40.0 | 15.0-35.0 | 20.0-30.0 | 22.0-28.0 | 22.5-27.5 |
| PEG-32 | 0.01-3.0 | 0.03-2.5 | 0.05-2.0 | 0.1-1.0 | 0.2-0.9 |
| Polyvinyl acetate | 0.01-3.0 | 0.03-2.5 | 0.05-2.0 | 0.1-1.0 | 0.2-0.9 |
| AFFINISOL HPCM HME 4M*** | 0.01-2.5 | 0.05-2.0 | 0.08-1.5 | 0.1-1.0 | 0.1-0.9 |
| Advantage L-CE**** | 0.01-3.0 | 0.03-2.5 | 0.05-2.0 | 0.1-1.0 | 0.2-0.9 |
| Diethyl ether | 50.0-90.0 | 55.0-85.0 | 60.0-80.0 | 65.0-75.0 | 65.5-74.5 |

*Cellulose
**Aqua, Ethylhexyl Acrylate/Methyl Methacrylate
***Hydroxyethylpropylmethylcellulose, Aqua (water), Sodium chloride
****Vinyl Caprolactam/VP/Dimethylaminoethyl Methacrylate Copolymer [(and) Lauryl Pyrrolidone]

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A hair styling composition comprising:
   a) at least one component comprising fibers,
   b) at least one polymer comprising an acrylate polymer, and
   c) at least one polymer comprising a polyurethane,
   wherein the at least one polymer comprising a polyurethane has at least two of the monomer units chosen from propylene glycol, ethylene glycol, 4,4-MDI, 2,4-MDI, 2,2-MDI and mixtures thereof.

2. Hair styling composition according to claim 1, wherein the at least one component comprising fibers is fibers produced from natural fiber materials.

3. Hair styling composition according to claim 1, wherein the at least one acrylate polymer is chosen from compounds with the INCI designation ethylhexyl acrylates/methyl methacrylate copolymer.

4. Hair styling composition according to claim 1, wherein the at least one component comprising fibers in present in an amount of from about 0.05 to about 5.0% by weight based on a total weight of the hair styling composition.

5. Hair styling composition according to claim 1, wherein the at least one polymer comprising an acrylate polymer is present in the hair styling composition in an amount from about 0.1 to about 10.0% by weight based on a total weight of the hair styling composition.

6. Hair styling composition according to claim 1, wherein the at least one polymer comprising a polyurethane is present in the hair styling composition in an amount from about 0.01 to about 5.5% by weight based on a total weight of the hair styling composition.

7. Hair styling composition according to claim 1, wherein the hair styling composition comprises at least one monohydric alcohol.

8. A hair styling composition comprising the composition according to claim 1 and a blowing agent.

9. A process for temporarily reshaping keratinous fibers, wherein a hair styling composition according to claim 1 is applied to keratinous fibers.

10. A hair styling composition comprising:
    a) at least one component comprising fibers chosen from cotton fibers, flax fibers, bamboo fibers, kapok fibers, and combinations thereof and present in an amount of about 0.5 to about 3.0% by weight based on a total weight of the hair styling composition,
    b) at least one polymer comprising an acrylate polymer chosen from compounds with the INCI designation ethylhexyl acrylates/methyl methacrylate copolymer and present in an amount of about 1.5 to about 6% by weight based on a total weight of the hair styling composition,
    c) at least one polymer comprising a polyurethane having at least three of the monomer units chosen from propylene glycol, ethylene glycol, 4,4-MDI, 2,4-MDI, 2,2-MDI and mixtures thereof and present in an amount of about 0.5 to about 4% by weight based on a total weight of the hair styling composition, and
    a monohydric alcohol chosen from methanol, ethanol, n-propanol, iso-propanol, n-butanol, isobutanol, tert-butanol, pentanol, and combinations thereof.

11. Hair styling composition according to claim 2, wherein the at least one acrylate polymer is chosen from compounds with the INCI designation ethylhexyl acrylates/methyl methacrylate copolymer.

12. Hair styling composition according to claim 2, wherein the at least one component comprising fibers in present in an amount of from about 0.05 to about 5.0% by weight based on a total weight of the hair styling composition.

13. Hair styling composition according to claim 3, wherein the at least one component comprising fibers in present in an amount of from about 0.05 to about 5.0% by weight based on a total weight of the hair styling composition.

14. Hair styling composition according to claim 2, wherein the at least one polymer comprising an acrylate polymer is present in the hair styling composition in an amount from about 0.1 to about 10.0% by weight based on a total weight of the hair styling composition.

15. Hair styling composition according to claim 3, wherein the at least one polymer comprising an acrylate polymer is present in the hair styling composition in an amount from about 0.1 to about 10.0% by weight based on a total weight of the hair styling composition.

16. Hair styling composition according to claim 4, wherein the at least one polymer comprising an acrylate polymer is present in the hair styling composition in an amount from about 0.1 to about 10.0% by weight based on a total weight of the hair styling composition.

17. Hair styling composition according to claim 2, wherein the at least one component comprising fibers in present in an amount of from about 0.05 to about 5.0% by weight based on a total weight of the hair styling composition, wherein the at least one polymer comprising an acrylate polymer is present in the hair styling composition in an amount from about 0.1 to about 10.0% by weight based on a total weight of the hair styling composition, and wherein the at least one polymer comprising a polyurethane is present in the hair styling composition in an amount from about 0.01 to about 5.5% by weight based on a total weight of the hair styling composition.

18. Hair styling composition according to claim 3, wherein the at least one component comprising fibers in present in an amount of from about 0.05 to about 5.0% by weight based on a total weight of the hair styling composition, wherein the at least one polymer comprising an acrylate polymer is present in the hair styling composition in an amount from about 0.1 to about 10.0% by weight based on a total weight of the hair styling composition, and wherein the at least one polymer comprising a polyurethane is present in the hair styling composition in an amount from about 0.01 to about 5.5% by weight based on a total weight of the hair styling composition.

* * * * *

UNITED STATES PATENT AND TRADEMARK OFFICE
CERTIFICATE OF CORRECTION

PATENT NO. : 11,638,680 B2
APPLICATION NO. : 17/123313
DATED : May 2, 2023
INVENTOR(S) : Diane Metten et al.

It is certified that error appears in the above-identified patent and that said Letters Patent is hereby corrected as shown below:

In the Specification

Column 11, Line 7 change "1,2,2-tetrachloro-1-fluoroethane" to --1,1,2,2-tetrachloro-1-fluoroethane--.

Column 11, Line 8 change "1,1,2-tetrachloro-2-fluoroethane" to --1,1,1,2- tetrachloro-2-fluoroethane--.

Column 11, Line 16 change "1-chloro-1,2-trifluoroethane" to --1-chloro-1,1,2-trifluoroethane--.

Column 11, Line 19 change "1-chloro fluoroethane 2-chloro-1" to --1-chloro-1-fluoroethane 2-chloro-1--.

Signed and Sealed this
Second Day of January, 2024

Katherine Kelly Vidal
*Director of the United States Patent and Trademark Office*